(12) United States Patent
Suzuki et al.

(10) Patent No.: US 8,188,007 B2
(45) Date of Patent: May 29, 2012

(54) HERBICIDE COMPOSITION FOR LAWN

(75) Inventors: Hisato Suzuki, Ibaraki (JP); Kiyoshi Taniguchi, Ibaraki (JP); Kumiko Taniguchi, legal representative, Ibaraki (JP); Hikari Taniguchi, legal representative, Ibaraki (JP); Akane Taniguchi, legal representative, Ibaraki (JP); Kunio Kihara, Ibaraki (JP)

(73) Assignee: Bayer Cropscience AG, Monheim (DE)

( * ) Notice: Subject to any disclaimer, the term of this patent is extended or adjusted under 35 U.S.C. 154(b) by 187 days.

(21) Appl. No.: 12/226,428

(22) PCT Filed: Mar. 30, 2007

(86) PCT No.: PCT/EP2007/002883
§ 371 (c)(1), (2), (4) Date: Oct. 13, 2009

(87) PCT Pub. No.: WO2007/121825
PCT Pub. Date: Nov. 1, 2007

(65) Prior Publication Data
US 2010/0184756 A1    Jul. 22, 2010

(30) Foreign Application Priority Data
Apr. 20, 2006    (JP) .................................. 2006-116578

(51) Int. Cl.
*A01N 43/64*    (2006.01)
*A01N 47/10*    (2006.01)

(52) U.S. Cl. .......................... 504/133; 504/134; 504/135

(58) Field of Classification Search .................. None
See application file for complete search history.

(56) References Cited

U.S. PATENT DOCUMENTS
7,799,343 B2 * 9/2010 Loughner .................... 424/489

FOREIGN PATENT DOCUMENTS
| CN | 1589624 | * | 3/2005 |
| EP | 0 661 001 | | 7/1995 |
| JP | 2004 026758 | | 1/2004 |

OTHER PUBLICATIONS

Derwent Publications Ltd., London, GB; AN 2004-207212, XP002481040.
James D. Morre "A 10-Year Evaluation of Plant Growth Regulator Carryover in Roadside Test Plots in Indiana" Journal of Plant Growth Regulation, 1993;12(2): 91-3.
Ikeda Osamu et al. "Development of a New Herbicide, Indanofan", Journal of Pesticide Science, 2004;29(2): 153-159, 139-140.

* cited by examiner

*Primary Examiner* — Alton Pryor
(74) *Attorney, Agent, or Firm* — Baker Donelson Bearman Caldwell & Berkowitz, P.C.

(57) ABSTRACT

A herbicide composition for lawn characterized by containing iodosulfuron-methyl or its salt, and at least 1 kind of herbicidal compound selected from the group consisting of oxaziclomefone, fentrazamide, oxadiargyl, ethoxysulfuron, cafenstrole, indanofan, asulam, fenoxaprop, clethodim, ethofumesate, tribenuron-methyl, metsulfuron-methyl, thifensulfuron-methyl, bromoxynil, MCPA, 2,4-D, dicamba as effective components.

18 Claims, No Drawings

HERBICIDE COMPOSITION FOR LAWN

CROSS REFERENCE TO RELATED APPLICATIONS

This application is a §371 National Stage Application of PCT/EP2007/002883 filed Mar. 30, 2007 which claims priority to Japanese Application 2006-116578 filed Apr. 20, 2006.

BACKGROUND OF THE INVENTION

1. Field of the Invention

The present invention relates to a herbicide composition for lawn. More specifically the present invention relates to a herbicide composition for lawn consisting of a combination of at least 2 kinds of specified herbicidal compounds.

2. Description of Related Art

4-Iodo-2-[3-(4-methoxy-6-methyl-1,3,5-triazin-2-yl)ureidosulfonyl]benzoic acid (common name: iodosulfuron-methyl),
3-[1-(3,5-dichlorophenyl)-1-methylethyl]-3,4-dihydro-6-methyl-5-phenyl-2H-1,3-oxazin-4-one (common name: oxaziclomefone),
4-(2-chlorophenyl)-N-cyclohexyl-N-ethyl-4,5-dihydro-5-oxo-1H-terazol-1-carboxamide (common name: fentrazamide),
5-tert-butyl-3-(2,4-dichloro-5-propargyloxyphenyl)-1,3,4-oxadiazol-2(3H)-one (common name: oxadiargyl),
N,N-diethyl-3-meticylsulfonyl-1H-1,2,4-triazol-1-carboxamide (common name: cafenstrole),
1-(4,6-dimethoxypyrimidin-2-yl)-3-(2-ethoxyphenoxysulfonyl)urea (common name: ethoxysulfuron),
(RS)-2-[2-(3-chlorophenyl)-2,3-epoxypropyl]-2-ethylindan-1,3-dione (common name: indanofan),
methyl sulfanyl carbamate (common name: asulam)
(±)-2-[4-(6-chloro-1,3-benzoxazol-2-yloxy)phenoxy]propionate; ethyl
(±)-2-[4-(6-chlorobenzoxazol-2-yloxy)phenoxy]propionate (common name: fenoxaprop),
(±)-2-[(E)-1-[(E)-3-chloroallyloxyimino]propyl]-5-[2-(ethylthio)propyl]-=3-hydroxycyclohex-2-enone (common name: clethodim),
(±)-2-ethoxy-2,3-dihydro-3,3-dimethylbenzofuran-5-yl methanesulfonate (common name: ethofumesate),
methyl 2-[4-methoxy-6-methyl-1,3,5-triazin-(2-yl(methyl)carbamoylsulfamoyl]-benzoate (common name: tribenuron-methyl),
methyl 2-(4-methoxy-6-methyl-1,3,5-triazin-2-ylcarbamoylsulfamoyl)benzoate (common name: metsulfuron-methyl),
methyl 3-(4-methoxy-6-methyl-1,3,5-triazin-1-ylcarbamoylsulfamoyl)thiophen-=2-carboxylate (common name: thifensulfuron-methyl),
3,5-dibromo-4-hydroxybenzonitrile; 3,5-dibromo-4-hydroxyphenyl cyanide (common name: bromoxynil),
(4-chloro-2-methylphenoxy)acetic acid; 4-chloro-o-tolyloxyacetic acid (common name: MCPA),
(2,4-dichlorophenoxy)acetic acid (common name: 2,4-D) and
3,6-dichloro-o-anisic acid (common name: dicamba), are known as herbicide (cf. The Pesticide Manual, 14th Edition, 2006, published by British Crop Protection Council).

Also a herbicide composition containing, for example, iodosulfuron-methyl and other herbicides for controlling rice weeds is known (cf. Japanese Laid-open Patent Publication No. 2002-520342).

Further, a mixed composition of at least 2 kinds of compounds selected from many known herbicides such as iodosulfuron-methyl, oxadiargyl, etc. is also known (cf. Japanese Laid-open Patent Publication No. 2005-502717).

In the lawn management for instance in a garden, golf course, public green areas, roadsides, etc., control of lawn weeds is the most important task for keeping views and good maintenance of golf course, etc. Up to now, however, there have been no satisfactory herbicides for lawn.

SUMMARY OF THE INVENTION

The present inventors found that the combination of the herbicidal compounds mentioned below shows an excellent and desirable effect in terms of weed controlling on the lawn and no or reduced phytotoxicity to the lawn and completed the present invention.

Thus, the present invention provides a herbicide for lawn characterized by combining
(a) iodosulfuron-methyl or its salt, and
(b) at least 1 kind of herbicidal compound selected from the group consisting of oxaziclomefone, fentrazamide, oxadiargyl, ethoxysulfuron, cafenstrole, indanofan, asulam, fenoxaprop, clethodim, ethofumesate, tribenuron-methyl, metsulfuron-methyl, thifensulfuron-methyl, bromoxynil, MCPA, 2,4-D and dicamba.

DETAILED DESCRIPTION OF A PREFERRED EMBODIMENT

In the present invention, the particularly preferable example of salt of iodosulfuron-methyl is the sodium salt.

The herbicides (a) and (b) are referred to either by the "common name" according to the International Organization for Standardization (ISO) or by the chemical name, if appropriate together with a customary code number and in each case include all application forms, such as acids, salts, esters and isomers, such as stereoisomers and optical isomers.

Preferred herbicides (b) are oxaziclomefone, fentrazamide, oxadiargyl, ethoxysulfuron, cafenstrole, indanofan and asulam.

The combined herbicide of the present invention, preferably, shows a substantially higher herbicidal effect (synergistic effect) than the sum of the effect of each active compound by each single application, compared with the case that each active compound of the above-mentioned (a) and (b) is used each singly. As a result, in case of controlling weeds, it is possible to substantially reduce the concentration of each substance used by now. At the same time, the combined herbicide of the present invention shows excellent controlling effect against a wide range of weeds on the lawn and gives no or reduced phytotoxicity to lawn species such as *cynodon* spp., *pasapalum notatum, zoysia* spp., *stenotaphrum americanum, axonopus* spp., *eremochloa optiuroides, pennisetum clandestinum, festuca rubra, festuca arundinacea, agrostis stolonifera, agrostis tenuis, poa pretense, lolium perenne.* Consequently, the combined herbicide of the present invention can be applied as an excellent, selective herbicide for the lawn.

In the combined herbicide of the present invention, the usage ratio of a component (a) and a component (b) is not strictly restricted but can be varied in a relatively wide range according to the application time, application place, application method, etc. of said combined herbicide. Generally, a herbicidal compound as the component (b) can be used in the range of 0.001-1000 parts by weight, preferably 0.01-100 parts by weight to 1 part by weight of a component (a). More specifically, as for the preferred components (b), there can be used the amounts, for example, in the following ranges to 1 part by weight of iodosulfuron-methyl sodium salt as the component (a):

(b-1) oxaziclomefone: 2-15 parts by weight, preferably 5-10 parts by weight,
(b-2) fentrazamide: 50-110 parts by weight, preferably 60-100 parts by weight,
(b-3) oxadiargyl: 5-15 parts by weight, preferably 7-12 parts by weight,
(b-4) ethoxysulfuron: 3-12 parts by weight, preferably 5-9 parts by weight,
(b-5) cafenstrole: 70-150 parts by weight, preferably 90-130 parts by weight,
(b-6) indanofan: 30-80 parts by weight, preferably 40-70 parts by weight,
(b-7) asulam: 50-110 parts by weight, preferably 60-100 parts by weight.

The combined herbicide of the present invention can be used for controlling various kinds of weeds developing on the lawn.

As examples of the weeds to be controlled there can be mentioned the following: Monocotyledonous weeds such as: *Digitaria ciliayis* (Retz.) Koeler, *Eleusine indica* (L.) Gaertn., *Setaria viridis* (L.) Beauv. var. *viridis, Poa annua* L., *Alopecurus aequalis* Sobol. var. *amurensis, Imperata cylindrica* (L.) Beau., *Luzula capitata* (Mig.) Mig, *Cyperus rotundus* L., *Cyperus brevifolius* (Rottb.) Hassk. var. *leiolepis, Digitaria radicosa* (Presl) Mig., *Digitaria* violascens Link), *Setaria faberii* Herrm, etc.

Dicotyledonous weeds such as: *Rumex japonicus* Houtt., *Portulaca oleracea* L. var. *oleracea, Stellaria neglecta Weihe, Kummerowia striata* (Thunb. ex Murray) Schindl., *Euphorbia supina* Rafin, *Galinsoga ciliata* (Rafin.) Blake, *Cerastium glomeratum* Thuill., *Stellaria alsine* Grimm. var. *undulata* (Thunb. ex Murray) Ohwi, *Cardamine flexuosa* With., *Capsella bursa-pastoris* Medicus, *Lamium amplexicaule* L., *Veronica persica* Poir., *Aster maaekii* Regel, *Oxalis corniculata* L., *Hydrocotyle sibthorpioides* Lam., *Plantago asiatica* L., *Plantago lanceolata* L., *Artemisia indica* Willd. var. *maximowiczii* (Nakai) Hara, *Erigeron philadelphicus* L., *Rumex acetosa* L., *Taraxacum officinale* Weber, etc.

The use of the combined herbicide of the present invention, however, should not be restricted to these weeds in any way, but can be applied against other weeds in the same manner.

The combined herbicide of the present invention can be made into customary formulation forms in case of using for control of lawn weeds. As such formulation forms there can be mentioned, for example, solutions, emulsions, wettable powders, suspensions, water dispersible granules, powders, soluble powders, granules, suspo-emulsion concentrates, microcapsules in polymer substance, etc.

These formulations can be prepared by per se known methods. The formulations according to the present invention can be prepared, for example, by mixing the aforementioned components (a) and (b) with extenders, namely liquid diluents and/or solid diluents, and, in case of necessity, by using surfactants, namely emulsifiers and/or dispersants.

In case of using water as extender, for example, organic solvents can be used as auxiliary solvent. As liquid diluents there can be mentioned, for example, organic solvents such as aromatic hydrocarbons (for example, xylene, toluene, alkylnaphthalene, etc.), chlorinated aromatic or chlorinated aliphatic hydrocarbons (for example, chlorobenzenes, ethylene chlorides, methylene chloride, etc.), aliphatic hydrocarbons [for example, cyclohexane etc. or paraffins (for example, mineral oil fractions, mineral oils, vegetable oils, etc.)], alcohols (for example, butanol, glycols and their ethers, esters, etc.), ketones (for example, acetone, methyl ethyl ketone, methyl isobutyl ketone, cyclohexanone, etc.), strongly polar solvents (for example, dimethylformamide, dimethyl sulfoxide, etc.), and water.

As solid diluents there can be mentioned, for example, ground natural minerals (for example, kaolin, clay, talc, chalk, quartz, attapulgite, montmorillonite, diatomaceous earth, etc.), ground synthetic minerals (for example, highly dispersed silicic acid, alumina, silicates, etc.) etc. As solid carriers for granules, for example, crushed and fractionated rocks (for example, calcite, marble, pumice, sepiolite, dolomite, etc.) synthetic granules of inorganic and organic meals, particles of organic materials (for example, saw dust, coconut shells, maize cobs, tobacco stalks, etc.) etc. can be used.

As surfactants there can be mentioned nonionic or anionic surfactants. As suitable nonionic surfactants there can be mentioned, for example, compounds obtained by addition polymerization of ethylene oxide to higher alcohols such as lauryl alcohol, stearyl alcohol, oleyl alcohol, etc.; compounds obtained by addition polymerization of ethylene oxide to alkylphenols such as isooctylphenol, nonylphenol, etc.; compounds obtained by addition polymerization of ethylene oxide to alkynaphthols such as butylnaphthol, octylnaphthol, etc.; compounds obtained by addition polymerization of ethylene oxide to higher fatty acids such as palmitic acid, stearic acid, oleic acid, etc.; compounds obtained by addition polymerization of ethylene oxide to amines such as dodecylamine, stearic acid amine, etc.; higher fatty acid esters of polyhydric alcohols such as sorbitan etc. and compounds obtained by addition polymerization of ethylene oxide thereto; compounds obtained by block addition polymerization of ethylene oxide and propylene oxide, etc. As suitable anionic surfactants there can be mentioned, for example, alkyl sulfate salts such as sodium lauryl sulfate, amine salt of oleyl alcohol sulfuric acid ester, etc.; alkylsulfonic acid salts such as sodium dioctylsulfosuccinate, sodium 2-ethylhexenesulfonate, etc.; arylsulfonic acid salts such as sodium isopropyl-naphthalenesulfonate, sodium methylenebis-naphthalenesulfonate, sodium lignin-sulfonate, sodium dodecylbenezenesulfonate, etc.

As dispersants, for example, lignin sulfite waste liquor or methyl cellulose are suitable.

Tackifiers can also be used in formulations (powders, granules, emulsifiable concentrates). As said tackifiers there can be mentioned, for example, carboxymethyl cellulose, natural and synthetic polymers (for example, gum Arabic, polyvinyl alcohol, polyvinyl acetates, etc.) natural phospholipids (for example, cephalins or recithins), synthetic phospholipids, etc. Further, as additives, mineral oils or vegetable oils can be used.

Colorants can also be used. As said colorants there can be mentioned inorganic pigments (for example, iron oxide, titanium oxide, Prussian Blue, etc,), organic dyestuffs such as alizarin dyestuffs, azo dyestuffs or metal phthalocyanine dyestuffs, and further traces nutrients such as salts of metals such as iron, manganese, boron, copper, cobalt, molybdenum, zinc, etc.

The formulations can contain the total of the aforementioned components (a) and (b) constituting the herbicide of the present invention at a concentration in the range of generally 0.1-95% by weight, preferably 0.5-90% by weight.

The herbicide of the present invention can be used for controlling weeds as themselves or in their formulation forms. It is also possible to do tank mixing at the time of usage and further to use together with other known active compounds, for example, other herbicides, safeners, fungicides, insecticides, plant growth regulators, plant nutrients or soil improving agents.

The herbicide of the present invention can be used as such or in their formulation forms or in application forms prepared by further diluting said formulations, for example, in the forms of ready-to-use solutions, emulsifiable concentrates, suspensions, powders, wettable powders, granules, etc. Formulations of these forms can be applied to lawn growing area by usual methods, for example, watering, spraying, atomizing, dusting, granule spreading, etc.

The application amount of the herbicide of the present invention can be varied in a substantial range according to, for example, the weeds to be controlled, application time, soil conditions, formulation form, etc. The application amount can be in the range of, for example, 0.0005 kg-50 kg/ha, preferably 0.001 kg-5 kg/ha as the total amount of the effective components of the components (a) and (b).

The herbicide of the present invention can be applied not only in the form of a mixed formulation containing the components (a) and (b) as mentioned above but also in the form of a single formulation of each component (a) and (b) simultaneously, continuously or successively.

The herbicide of the present invention shows, as shown in the below-mentioned test examples, a precise controlling effect against various kinds of lawn weeds and shows an excellent residual effect.

Excellent effect of the herbicide of the present invention will be described more specifically by the following examples. The present invention, however, should not be restricted only to them in any way. In the examples the component (a) and components (b-1)-(b-7) are defined as aforementioned.

EXAMPLES

Formulation Examples

Example 1

Flowable

| | |
|---|---|
| Component (a) | 1.7% by weight |
| Component (b-1) | 15.0% by weight |
| Polyoxyethylene nonyl phenyl ether | 2.0% by weight |
| Sodium dioctylsulfosuccinate | 2.0% by weight |
| Xanthan gum | 0.2% by weight |
| Water | 79.1% by weight |

The above-mentioned components are wet crushed with a wet ball mill to obtain a flowable.

Example 2

Granule

| | |
|---|---|
| Component (a) | 1.7% by weight |
| Component (b-1) | 15.0% by weight |
| Sodium ligninsulfonate | 3.0% by weight |
| Sodium alkylnaphthalenesulfonate | 1.0% by weight |
| Bentonite | 30.0% by weight |
| Talc | 49.3% by weight |

After the above-mentioned components have been mixed and crushed, the mixture is granulated by a usual method with a granulator and dried to obtain granules.

Example 3

Wettable Powder

| | |
|---|---|
| Component (a) | 1.7% by weight |
| Component (b-1) | 15.0% by weight |
| Sodium ligninsulfonate | 3.0% by weight |
| Sodium dialkyl naphthalenesulfonate | 3.0% by weight |
| Kaolin | 77.3% by weight |

The above-mentioned components are mixed, crushed and homogenized to obtain a wettable powder.

Example 4

Flowable

| | |
|---|---|
| Component (a) | 0.34% by weight |
| Component (b-2) | 30.0% by weight |
| Polyoxyethylene nonyl phenyl ether | 2.0% by weight |
| Sodium dioctylsulfosuccinate | 2.0% by weight |
| Xanthan gum | 0.2% by weight |
| Water | 65.46% by weight |

The above-mentioned components are wet crushed with a wet ball mill to obtain a flowable.

Example 5

Granule

| | |
|---|---|
| Component (a) | 0.17% by weight |
| Component (b-2) | 15.0% by weight |
| Sodium ligninsulfonate | 3.0% by weight |
| Sodium alkylnaphthalenesulfonate | 1.0% by weight |
| Bentonite | 30.0% by weight |
| Talc | 50.83% by weight |

After the above-mentioned components have been mixed and crushed, the mixture is granulated by a usual method with a granulator and dried to obtain granules.

Example 6

Wettable Powder

| | |
|---|---|
| Component (a) | 0.34% by weight |
| Component (b-2) | 30.0% by weight |
| Sodium ligninsulfonate | 3.0% by weight |
| Sodium dialkyl naphthalenesulfonate | 3.0% by weight |
| Kaolin | 63.66% by weight |

The above-mentioned components are mixed, crushed and homogenized to obtain a wettable powder.

Example 7

Flowable

| | |
|---|---|
| Component (a) | 1.7% by weight |
| Component (b-3) | 17.0% by weight |
| Polyoxyethylene nonyl phenyl ether | 2.0% by weight |
| Sodium dioctylsulfosuccinate | 2.0% by weight |
| Xanthan gum | 0.2% by weight |
| Water | 77.1% by weight |

The above-mentioned components are wet crushed with a wet ball mill to obtain a flowable.

Example 8

Granule

| | |
|---|---|
| Component (a) | 1.7% by weight |
| Component (b-3) | 17.0% by weight |
| Sodium ligninsulfonate | 3.0% by weight |
| Sodium alkylnaphthalenesulfonate | 1.0% by weight |
| Bentonite | 30.0% by weight |
| Talc | 47.3% by weight |

After the above-mentioned components have been mixed and crushed, the mixture is granulated by a usual method with a granulator and dried to obtain granules.

Example 9

Wettable Powder

| | |
|---|---|
| Component (a) | 1.7% by weight |
| Component (b-3) | 17.0% by weight |
| Sodium ligninsulfonate | 3.0% by weight |
| Sodium dialkyl naphthalenesulfonate | 3.0% by weight |
| Kaolin | 75.3% by weight |

The above-mentioned components are mixed, crushed and homogenized to obtain a wettable powder.

Example 10

Flowable

| | |
|---|---|
| Component (a) | 1.7% by weight |
| Component (b-4) | 12.5% by weight |
| Polyoxyethylene nonyl phenyl ether | 2.0% by weight |
| Sodium dioctylsulfosuccinate | 2.0% by weight |
| Xanthan gum | 0.2% by weight |
| Water | 81.6% by weight |

The above-mentioned components are wet crushed with a wet ball mill to obtain a flowable.

Example 11

Granule

| | |
|---|---|
| Component (a) | 1.7% by weight |
| Component (b-4) | 12.5% by weight |
| Sodium ligninsulfonate | 3.0% by weight |
| Sodium alkylnaphthalenesulfonate | 1.0% by weight |
| Bentonite | 30.0% by weight |
| Talc | 51.8% by weight |

After the above-mentioned components have been mixed and crushed, the mixture is granulated by a usual method with a granulator and dried to obtain granules.

Example 12

Wettable Powder

| | |
|---|---|
| Component (a) | 1.7% by weight |
| Component (b-4) | 12.5% by weight |
| Sodium ligninsulfonate | 3.0% by weight |
| Sodium dialkyl naphthalenesulfonate | 3.0% by weight |
| Kaolin | 79.8% by weight |

The above-mentioned components are mixed, crushed and homogenized to obtain a wettable powder.

Example 13

Flowable

| | |
|---|---|
| Component (a) | 0.34% by weight |
| Component (b-5) | 40.0% by weight |
| Polyoxyethylene nonyl phenyl ether | 2.0% by weight |
| Sodium dioctylsulfosuccinate | 2.0% by weight |
| Xanthan gum | 0.2% by weight |
| Water | 55.46% by weight |

The above-mentioned components are wet crushed with a wet ball mill to obtain a flowable.

Example 14

Granule

| | |
|---|---|
| Component (a) | 0.17% by weight |
| Component (b-5) | 20.0% by weight |
| Sodium ligninsulfonate | 3.0% by weight |
| Sodium alkylnaphthalenesulfonate | 1.0% by weight |
| Bentonite | 30.0% by weight |
| Talc | 45.83% by weight |

After the above-mentioned components have been mixed and crushed, the mixture is granulated by a usual method with a granulator and dried to obtain granules.

Example 15

Wettable Powder

| | |
|---|---|
| Component (a) | 0.34% by weight |
| Component (b-5) | 40.0% by weight |
| Sodium ligninsulfonate | 3.0% by weight |
| Sodium dialkyl naphthalenesulfonate | 3.0% by weight |
| Kaolin | 53.66% by weight |

The above-mentioned components are mixed, crushed and homogenized to obtain a wettable powder.

Example 16

Flowable

| | |
|---|---|
| Component (a) | 0.34% by weight |
| Component (b-6) | 20.0% by weight |
| Polyoxyethylene nonyl phenyl ether | 2.0% by weight |
| Sodium dioctylsulfosuccinate | 2.0% by weight |
| Xanthan gum | 0.2% by weight |
| Water | 75.46% by weight |

The above-mentioned components are wet crushed with a wet ball mill to obtain a flowable.

Example 17

Granule

| | |
|---|---|
| Component (a) | 0.34% by weight |
| Component (b-6) | 20.0% by weight |
| Sodium ligninsulfonate | 3.0% by weight |
| Sodium alkylnaphthalenesulfonate | 1.0% by weight |
| Bentonite | 30.0% by weight |
| Talc | 45.66% by weight |

After the above-mentioned components have been mixed and crushed, the mixture is granulated by a usual method with a granulator and dried to obtain granules.

Example 18

Wettable Powder

| | |
|---|---|
| Component (a) | 0.34% by weight |
| Component (b-6) | 20.0% by weight |
| Sodium ligninsulfonate | 3.0% by weight |
| Sodium dialkyl naphthalenesulfonate | 3.0% by weight |
| Kaolin | 73.66% by weight |

The above-mentioned components are mixed, crushed and homogenized to obtain a wettable powder.

Example 19

Flowable

| | |
|---|---|
| Component (a) | 0.34% by weight |
| Component (b-7) | 30.0% by weight |
| Polyoxyethylene nonyl phenyl ether | 2.0% by weight |
| Sodium dioctylsulfosuccinate | 2.0% by weight |
| Xanthan gum | 0.2% by weight |
| Water | 65.46% by weight |

The above-mentioned components are wet crushed with a wet ball mill to obtain a flowable.

Example 20

Granule

| | |
|---|---|
| Component (a) | 0.34% by weight |
| Component (b-7) | 30.0% by weight |
| Sodium ligninsulfonate | 3.0% by weight |
| Sodium alkylnaphthalenesulfonate | 1.0% by weight |
| Bentonite | 30.0% by weight |
| Talc | 35.66% by weight |

After the above-mentioned components have been mixed and crushed, the mixture is granulated by a usual method with a granulator and dried to obtain granules.

Example 21

Wettable Powder

| | |
|---|---|
| Component (a) | 0.34% by weight |
| Component (b-7) | 30.0% by weight |
| Sodium ligninsulfonate | 3.0% by weight |
| Sodium dialkyl naphthalenesulfonate | 3.0% by weight |
| Kaolin | 63.66% by weight |

The above-mentioned components are mixed, crushed and homogenized to obtain a wettable powder.

BIOLOGICAL EXAMPLES

Test Example 1

The Agent Amount Reduction Effect and Herbicidal Effect Enhancing Action of the Soil Treatment by Mixing On a field of Zoysia japonica sectioned to 100 cm×100 cm, seeds of *Digitaria* ciliayis (Retz.) Koeler, *Poa annua* L.,

*Polygonum hydropiper* L., *Euphorbia supine* Rafin, *Oxalis corniculata* L., *Cyperus microiria* were sown and covered with 0.5 cm soil. Seven days after weeds sowing, treatment was conducted with watering amount of 200 cc/m$^2$. The prescribed amount of test compound was sprayed with a small spray in the form of the formulation prepared according to the above-mentioned examples or a wettable powder of a single compound diluted with water.

The herbicidal effect and the degree of phytotoxicity to the lawn were studied 45 days after the agent treatment. The results are shown in Table 1 Table 7.

Evaluation Standard:
Herbicidal effect: 100%: complete death 0%: no effect
Phytotoxicity: 100%: complete death 0%: no phytotoxicity
In the tables, ai means the effective component.

TABLE 1

| | Effective component amount g ai/ha | | Herbicidal effect | | | | | | |
|---|---|---|---|---|---|---|---|---|---|
| Test agent | Iodosulfuron methyl sodium salt | Oxazi-clomefone | *Digitaria ciliayis* (Retz.) Koeler | *Poa annua* L. | *Polygonum blumei* | *Erigeron canadensis* | *Oxalis corniculata* L. | *Chenopodium ficifolium* | *Zoysia matrella* phytotoxicity |
| Iodosulfuron methyl sodium salt | 17 | — | 60 | 60 | 100 | 75 | 70 | 80 | 0 |
| Oxaziclomefone | — | 150 | 90 | 90 | 0 | 0 | 0 | 0 | 0 |
| Herbicide of the present invention | 8.5 | 75 | 95 | 100 | 100 | 100 | 100 | 100 | 0 |
| | 17 | 150 | 100 | 100 | 100 | 100 | 100 | 100 | 0 |
| | 25.5 | 225 | 100 | 100 | 100 | 100 | 100 | 100 | 0 |
| No treatment | — | — | 0 | 0 | 0 | 0 | 0 | 0 | 0 |

TABLE 2

| | Effective component amount g ai/ha | | Herbicidal effect | | | | | | |
|---|---|---|---|---|---|---|---|---|---|
| Test agent | Iodosulfuron methyl sodium salt | Fentrazamide | *Digitaria ciliayis* (Retz.) Koeler | *Poa annua* L. | *Polygonum blumei* | *Erigeron canadensis* | *Oxalis corniculata* L. | *Chenopodium ficifolium* | *Zoysia matrella* phytotoxicity |
| Iodosulfuron methyl sodium salt | 17 | — | 60 | 60 | 100 | 75 | 70 | 80 | 0 |
| Fentrazamide | — | 1500 | 90 | 80 | 0 | 0 | 0 | 20 | 0 |
| Herbicide of the present invention | 8.5 | 750 | 95 | 100 | 100 | 100 | 100 | 100 | 0 |
| | 17 | 1500 | 100 | 100 | 100 | 100 | 100 | 100 | 0 |
| | 25.5 | 2250 | 100 | 100 | 100 | 100 | 100 | 100 | 0 |
| No treatment | — | — | 0 | 0 | 0 | 0 | 0 | 0 | 0 |

TABLE 3

| | Effective component amount g ai/ha | | Herbicidal effect | | | | | | |
|---|---|---|---|---|---|---|---|---|---|
| Test agent | Iodosulfuron methyl sodium salt | Oxadiargyl | *Digitaria ciliayis* (Retz.) Koeler | *Poa annua* L. | *Polygonum blumei* | *Erigeron canadensis* | *Oxalis corniculata* L. | *Chenopodium ficifolium* | *Zoysia matrella* phytotoxicity |
| Iodosulfuron methyl sodium salt | 17 | — | 60 | 60 | 100 | 75 | 70 | 80 | 0 |
| Oxadiargyl | — | 170 | 70 | 70 | 40 | 20 | 20 | 50 | 0 |
| Herbicide of the present invention | 8.5 | 85 | 98 | 100 | 100 | 100 | 100 | 100 | 0 |
| | 17 | 170 | 100 | 100 | 100 | 100 | 100 | 100 | 0 |
| | 25.5 | 225 | 100 | 100 | 100 | 100 | 100 | 100 | 0 |
| No treatment | — | — | 0 | 0 | 0 | 0 | 0 | 0 | 0 |

TABLE 4

| Test agent | Effective component amount g ai/ha | | Herbicidal effect | | | | | | |
|---|---|---|---|---|---|---|---|---|---|
| | Iodosulfuron methyl sodium salt | Ethoxysulfuron | Digitaria ciliayis (Retz.) Koeler | Poa annua L. | Polygonum blumei | Erigeron canadensis | Oxalis corniculata L. | Chenopodium ficifolium | Zoysia matrella phytotoxicity |
| Iodosulfuron methyl sodium salt | 17 | — | 60 | 60 | 100 | 75 | 70 | 80 | 0 |
| Ethoxysulfuron | — | 125 | 0 | 0 | 60 | 75 | 50 | 70 | 0 |
| Herbicide of the present invention | 8.5 | 62.5 | 100 | 100 | 100 | 100 | 100 | 100 | 0 |
| | 17 | 120 | 100 | 100 | 100 | 100 | 100 | 100 | 0 |
| | 25.5 | 182.5 | 100 | 100 | 100 | 100 | 100 | 100 | 0 |
| No treatment | — | — | 0 | 0 | 0 | 0 | 0 | 0 | 0 |

TABLE 5

| Test agent | Effective component amount g ai/ha | | Herbicidal effect | | | | | | |
|---|---|---|---|---|---|---|---|---|---|
| | Iodosulfuron methyl sodium salt | Cafenstrole | Digitaria ciliayis (Retz.) Koeler | Poa annua L. | Polygonum blumei | Erigeron canadensis | Oxalis corniculata L. | Chenopodium ficifolium | Zoysia matrella phytotoxicity |
| Iodosulfuron methyl sodium salt | 17 | — | 60 | 60 | 100 | 75 | 70 | 80 | 0 |
| Cafenstrole | — | 2000 | 0 | 0 | 60 | 75 | 50 | 70 | 0 |
| Herbicide of the present invention | 8.5 | 1000 | 80 | 80 | 100 | 100 | 100 | 100 | 0 |
| | 17 | 2000 | 100 | 95 | 100 | 100 | 100 | 100 | 0 |
| | 25.5 | 3000 | 100 | 100 | 100 | 100 | 100 | 100 | 0 |
| No treatment | — | — | 0 | 0 | 0 | 0 | 0 | 0 | 0 |

TABLE 6

| Test agent | Effective component amount g ai/ha | | Herbicidal effect | | | | | | |
|---|---|---|---|---|---|---|---|---|---|
| | Iodosulfuron methyl sodium salt | Indanofan | Digitaria ciliayis (Retz.) Koeler | Poa annua L. | Polygonum blumei | Erigeron canadensis | Oxalis corniculata L. | Chenopodium ficifolium | Zoysia matrella phytotoxicity |
| Iodosulfuron methyl sodium salt | 17 | — | 60 | 60 | 100 | 75 | 70 | 80 | 0 |
| Indanofan | — | 1000 | 0 | 0 | 60 | 75 | 50 | 70 | 0 |
| Herbicide of the present invention | 8.5 | 500 | 80 | 80 | 100 | 100 | 100 | 100 | 0 |
| | 17 | 1000 | 90 | 90 | 100 | 100 | 100 | 100 | 0 |
| | 25.5 | 1500 | 100 | 100 | 100 | 100 | 100 | 100 | 0 |
| No treatment | — | — | 0 | 0 | 0 | 0 | 0 | 0 | 0 |

TABLE 7

| Test agent | Effective component amount g ai/ha | | Herbicidal effect | | | | | | |
|---|---|---|---|---|---|---|---|---|---|
| | Iodosulfuron methyl sodium salt | Asulam | Digitaria ciliayis (Retz.) Koeler | Poa annua L. | Polygonum blumei | Erigeron canadensis | Oxalis corniculata L. | Chenopodium ficifolium | Zoysia matrella phytotoxicity |
| Iodosulfuron methyl sodium salt | 17 | — | 40 | 50 | 80 | 75 | 50 | 70 | 0 |
| Asulam | — | 1500 | 20 | 20 | 0 | 0 | 0 | 0 | 0 |
| Herbicide of the present | 8.5 | 750 | 100 | 100 | 100 | 100 | 100 | 100 | 0 |
| | 17 | 1500 | 95 | 100 | 100 | 100 | 100 | 100 | 0 |

TABLE 7-continued

| Test agent | Effective component amount g ai/ha | | Herbicidal effect | | | | | | |
|---|---|---|---|---|---|---|---|---|---|
| | Iodosulfuron methyl sodium salt | Asulam | Digitaria ciliayis (Retz.) Koeler | Poa annua L. | Polygonum blumei | Erigeron canadensis | Oxalis corniculata L. | Chenopodium ficifolium | Zoysia matrella phytotoxicity |
| invention | 25.5 | 2250 | 100 | 100 | 100 | 100 | 100 | 100 | 0 |
| No treatment | — | ( | 0 | 0 | 0 | 0 | 0 | 0 | 0 |

Test Example 2

The Agent Amount Reduction Effect and Herbicidal Effect Enhancing Action of the Foliage and Soil Treatment by Mixing A test section of *Zoysia matrella* had been prepared in the same method as in the Test Example 1 and on the 28th day after weeds sowing a treatment was conducted with watering amount of 200 cc/m2. The prescribed amount of test compound was sprayed with a small spray in the form of the formulation prepared according to the aforementioned examples or a wettable powder of a single compound diluted with water.

The herbicidal effect and the degree of phytotoxicity to the lawn were studied 45 days after the agent treatment in the same manner as Test Example 1. The results are shown in Table 8-Table 14.

TABLE 8

| Test agent | Effective component amount g ai/ha | | Herbicidal effect | | | | | | |
|---|---|---|---|---|---|---|---|---|---|
| | Iodosulfuron methyl sodium salt | Oxaziclomefone | Digitaria ciliayis (Retz.) Koeler | Poa annua L. | Polygonum blumei | Erigeron canadensis | Oxalis corniculata L. | Chenopodium ficifolium | Zoysia matrella phytotoxicity |
| Iodosulfuron methyl sodium salt | 17 | — | 40 | 50 | 80 | 75 | 50 | 70 | 0 |
| Oxaziclomefone | — | 150 | 30 | 30 | 0 | 0 | 0 | 0 | 0 |
| Herbicide of the present invention | 8.5 | 75 | 90 | 95 | 100 | 90 | 90 | 100 | 0 |
| | 17 | 150 | 95 | 100 | 100 | 100 | 100 | 100 | 0 |
| | 25.5 | 225 | 100 | 100 | 100 | 100 | 100 | 100 | 0 |
| No treatment | — | — | 0 | 0 | 0 | 0 | 0 | 0 | 0 |

TABLE 9

| Test agent | Effective component amount g ai/ha | | Herbicidal effect | | | | | | |
|---|---|---|---|---|---|---|---|---|---|
| | Iodosulfuron methyl sodium salt | Fentrazamide | Digitaria ciliayis (Retz.) Koeler | Poa annua L. | Polygonum blumei | Erigeron canadensis | Oxalis corniculata L. | Chenopodium ficifolium | Zoysia matrella phytotoxicity |
| Iodosulfuron methyl sodium salt | 17 | — | 40 | 50 | 80 | 75 | 50 | 70 | 0 |
| Fentrazamide | — | 1500 | 40 | 30 | 0 | 0 | 0 | 0 | 0 |
| Herbicide of the present invention | 8.5 | 750 | 90 | 90 | 100 | 90 | 90 | 100 | 0 |
| | 17 | 1500 | 95 | 100 | 100 | 100 | 100 | 100 | 0 |
| | 25.5 | 2250 | 100 | 100 | 100 | 100 | 100 | 100 | 0 |
| No treatment | — | — | 0 | 0 | 0 | 0 | 0 | 0 | 0 |

TABLE 10

| Test agent | Effective component amount g ai/ha | | Herbicidal effect | | | | | | |
|---|---|---|---|---|---|---|---|---|---|
| | Iodosulfuron methyl sodium salt | Oxadiargyl | Digitaria ciliayis (Retz.) Koeler | Poa annua L. | Polygonum blumei | Erigeron canadensis | Oxalis corniculata L. | Chenopodium ficifolium | Zoysia matrella phytotoxicity |
| Iodosulfuron methyl sodium salt | 17 | — | 40 | 50 | 80 | 75 | 50 | 70 | 0 |

TABLE 10-continued

| Test agent | Effective component amount g ai/ha | | Herbicidal effect | | | | | | |
|---|---|---|---|---|---|---|---|---|---|
| | Iodosulfuron methyl sodium salt | Oxadiargyl | *Digitaria ciliayis* (Retz.) Koeler | *Poa annua* L. | *Polygonum blumei* | *Erigeron canadensis* | *Oxalis corniculata* L. | *Chenopodium ficifolium* | *Zoysia matrella* phytotoxicity |
| Oxadiargyl | — | 170 | 40 | 30 | 20 | 20 | 0 | 30 | 0 |
| Herbicide of the present invention | 8.5 | 85 | 90 | 90 | 90 | 90 | 90 | 100 | 0 |
| | 17 | 170 | 100 | 95 | 100 | 100 | 100 | 100 | 0 |
| | 25.5 | 225 | 100 | 100 | 100 | 100 | 100 | 100 | 0 |
| No treatment | — | — | 0 | 0 | 0 | 0 | 0 | 0 | 0 |

TABLE 11

| Test agent | Effective component amount g ai/ha | | Herbicidal effect | | | | | | |
|---|---|---|---|---|---|---|---|---|---|
| | Iodosulfuron methyl sodium salt | Ethoxysulfuron | *Digitaria ciliayis* (Retz.) Koeler | *Poa annua* L. | *Polygonum blumei* | *Erigeron canadensis* | *Oxalis corniculata* L. | *Chenopodium ficifolium* | *Zoysia matrella* phytotoxicity |
| Iodosulfuron methyl sodium salt | 17 | — | 40 | 50 | 80 | 75 | 50 | 70 | 0 |
| Ethoxysulfuron | — | 125 | 0 | 0 | 40 | 60 | 30 | 50 | 0 |
| Herbicide of the present invention | 8.5 | 62.5 | 90 | 90 | 95 | 100 | 100 | 100 | 0 |
| | 17 | 120 | 100 | 95 | 100 | 100 | 100 | 100 | 0 |
| | 25.5 | 182.5 | 100 | 100 | 100 | 100 | 100 | 100 | 0 |
| No treatment | — | — | 0 | 0 | 0 | 0 | 0 | 0 | 0 |

TABLE 12

| Test agent | Effective component amount g ai/ha | | Herbicidal effect | | | | | | |
|---|---|---|---|---|---|---|---|---|---|
| | Iodosulfuron methyl sodium salt | Cafenstrole | *Digitaria ciliayis* (Retz.) Koeler | *Poa annua* L. | *Polygonum blumei* | *Erigeron canadensis* | *Oxalis corniculata* L. | *Chenopodium ficifolium* | *Zoysia matrella* phytotoxicity |
| Iodosulfuron methyl sodium salt | 17 | — | 40 | 50 | 80 | 75 | 50 | 70 | 0 |
| Cafenstrole | — | 2000 | 40 | 30 | 0 | 0 | 0 | 20 | 0 |
| Herbicide of the present invention | 8.5 | 1000 | 80 | 80 | 90 | 90 | 90 | 90 | 0 |
| | 17 | 2000 | 100 | 95 | 100 | 100 | 100 | 100 | 0 |
| | 25.5 | 3000 | 100 | 100 | 100 | 100 | 100 | 100 | 0 |
| No treatment | — | — | 0 | 0 | 0 | 0 | 0 | 0 | 0 |

TABLE 13

| Test agent | Effective component amount g ai/ha | | Herbicidal effect | | | | | | |
|---|---|---|---|---|---|---|---|---|---|
| | Iodosulfuron methyl sodium salt | Indanofan | *Digitaria ciliayis* (Retz.) Koeler | *Poa annua* L. | *Polygonum blumei* | *Erigeron canadensis* | *Oxalis corniculata* L. | *Chenopodium ficifolium* | *Zoysia matrella* phytotoxicity |
| Iodosulfuron methyl sodium salt | 17 | — | 40 | 50 | 80 | 75 | 50 | 70 | 0 |
| Indanofan | — | 1000 | 30 | 30 | 0 | 0 | 0 | 20 | 0 |
| Herbicide of the present invention | 8.5 | 500 | 80 | 80 | 90 | 80 | 90 | 90 | 0 |
| | 17 | 1000 | 90 | 90 | 100 | 100 | 100 | 100 | 0 |
| | 25.5 | 1500 | 100 | 100 | 100 | 100 | 100 | 100 | 0 |
| No treatment | — | — | 0 | 0 | 0 | 0 | 0 | 0 | 0 |

TABLE 14

| Test agent | Effective component amount g ai/ha | | Herbicidal effect | | | | | | |
|---|---|---|---|---|---|---|---|---|---|
| | Iodosulfuron methyl sodium salt | Asulam | Digitaria ciliayis (Retz.) Koeler | Poa annua L. | Polygonum blumei | Erigeron canadensis | Oxalis corniculata L. | Chenopodium ficifolium | Zoysia matrella phytotoxicity |
| Iodosulfuron methyl sodium salt | 17 | — | 40 | 50 | 80 | 75 | 50 | 70 | 0 |
| Asulam | — | 1500 | 40 | 30 | 70 | 60 | 60 | 60 | 0 |
| Herbicide of the present invention | 8.5 | 750 | 100 | 100 | 100 | 100 | 100 | 100 | 0 |
| | 17 | 1500 | | 100 | 100 | 100 | 100 | 100 | 0 |
| | 25.5 | 2250 | 100 | 100 | 100 | 100 | 100 | 100 | 0 |
| No treatment | — | — | 0 | 0 | 0 | 0 | 0 | 0 | 0 |

The invention claimed is:

1. A method for controlling weeds in lawn, comprising applying to lawn a synergistic composition comprising
   (a) iodosulfuron-methyl or salt thereof, and
   (b) at least one herbicidal compound selected from the group consisting of oxaziclomefone, fentrazamide, oxadiargyl, ethoxysulfuron, cafenstrole, indanofan, and asulam.

2. The method of claim 1, wherein said iodosulfuron-methyl or salt thereof is a sodium salt.

3. The method of claim 1, wherein said herbicidal compound is oxaziclomefone.

4. The method of claim 1, wherein said herbicidal compound is fentrazamide.

5. The method of claim 1, wherein said herbicidal compound is oxadiargyl.

6. The method of claim 1, wherein said herbicidal compound is ethoxysulfuron.

7. The method of claim 1, wherein said herbicidal compound is cafenstrole.

8. The method of claim 1, wherein said herbicidal compound is indanofan.

9. The method of claim 1, wherein said herbicidal compound is asulam.

10. A synergistic composition for controlling weeds in lawn, said composition comprising
    (a) iodosulfuron-methyl or salt thereof, and
    (b) at least one herbicidal compound selected from the group consisting of oxaziclomefone, fentrazamide, oxadiargyl, ethoxysulfuron, cafenstrole, indanofan, and asulam.

11. The composition of claim 10, wherein said iodosulfuron-methyl or salt thereof is a sodium salt.

12. The composition of claim 10, wherein said herbicidal compound is oxaziclomefone.

13. The composition of claim 10, wherein said herbicidal compound is fentrazamide.

14. The composition of claim 10, wherein said herbicidal compound is oxadiargyl.

15. The composition of claim 10, wherein said herbicidal compound is ethoxysulfuron.

16. The composition of claim 10, wherein said herbicidal compound is cafenstrole.

17. The composition of claim 10, wherein said herbicidal compound is indanofan.

18. The composition of claim 10, wherein said herbicidal compound is asulam.

* * * * *